United States Patent
Liang et al.

(10) Patent No.: US 11,193,000 B2
(45) Date of Patent: *Dec. 7, 2021

(54) REVERSIBLE SELF-REPAIRING EPOXY RESIN AND PREPARATION AND RECOVERY REMOULDING METHOD THEREFOR

(71) Applicant: SOOCHOW UNIVERSITY, Suzhou (CN)

(72) Inventors: Guozheng Liang, Suzhou (CN); Youhao Zhang, Suzhou (CN); Aijuan Gu, Suzhou (CN); Li Yuan, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/759,327

(22) PCT Filed: Feb. 27, 2018

(86) PCT No.: PCT/CN2018/077462
§ 371 (c)(1),
(2) Date: Apr. 25, 2020

(87) PCT Pub. No.: WO2019/165583
PCT Pub. Date: Sep. 6, 2019

(65) Prior Publication Data
US 2020/0283595 A1    Sep. 10, 2020

(51) Int. Cl.
*C08J 11/12*    (2006.01)
*C07D 327/00*    (2006.01)
*C08G 59/42*    (2006.01)

(52) U.S. Cl.
CPC ............. *C08J 11/12* (2013.01); *C07D 327/00* (2013.01); *C08G 59/423* (2013.01); *C08J 2363/00* (2013.01)

(58) Field of Classification Search
CPC ..... C08J 11/12; C08J 2363/00; C07D 327/00; C08G 59/423
USPC .......................................................... 521/40
See application file for complete search history.

(56) References Cited

U.S. PATENT DOCUMENTS

| | | | |
|---|---|---|---|
| 5,863,998 A * | 1/1999 | Cai ......................... | C08F 20/28 526/318.2 |
| 2008/0220483 A1* | 9/2008 | Lee ........................ | C07C 331/28 435/106 |

(Continued)

FOREIGN PATENT DOCUMENTS

| | | |
|---|---|---|
| CN | 101153108 A | 4/2008 |
| CN | 101508823 A | 8/2009 |

(Continued)

OTHER PUBLICATIONS

Ghorbani-Choghamarani et al., "In situ generated hypoiodous acid in an efficient and heterogeneous catalytic system for the homo-oxidative coupling of thiols", Journal of the Serbian Chemical Society, 2013, vol. 78, No. 2, p. 173-178 (Year: 2013).*

(Continued)

*Primary Examiner* — David T Karst
(74) *Attorney, Agent, or Firm* — SZDC Law P.C.

(57) ABSTRACT

This invention provides a self-healable epoxy resin and its preparation, recycling and remolding method. With the catalyst of potassium iodide, an ester solution of 2-mercaptoacetic acid was oxidated by 30% $H_2O_2$ to form 2,2'-dithiodiacetic acid; then 2,2'-dithiodiacetic acid was dehydrated and cyclizated by anhydride to form 1,4,5-oxadithiepane-2,7-dione; 1,4,5-oxadithiepane-2,7-dione and methylhexahydrophthalic anhydride were mixed by mass ratio and cured with epoxides to get the self-healable epoxy resin. Through controlling dynamic and permanent three-dimensional crosslinked network, the self-healable epoxy resins provided in this invention exhibit high thermal resis- (Continued)

tance and improved mechanical properties as well as excellent self-healing ability, recyclability and remoldability. This invention provides a preparation method with the merits of low cost, simple production processes, broad application prospects and strong utility.

3 Claims, 7 Drawing Sheets

(56) References Cited

U.S. PATENT DOCUMENTS

| | | |
|---|---|---|
| 2012/0009145 A1 | 1/2012 | Slobodkin et al. |
| 2012/0136125 A1 | 5/2012 | Rousseau |

FOREIGN PATENT DOCUMENTS

| | | |
|---|---|---|
| CN | 105288648 A | 2/2016 |
| CN | 105682936 A | 6/2016 |
| CN | 105833284 A | 8/2016 |
| CN | 106589819 A | 4/2017 |
| CN | 106729746 A | 5/2017 |
| CN | 1084440740 A | 8/2018 |

OTHER PUBLICATIONS

Robert et al., "Facile and Efficient Synthesis of Cyclic Anhydrides from Dicarboxylic Acids", ACS Catalysis, 2014, vol. 4, p. 3586-3589 (Year: 2014).*

* cited by examiner

REVERSIBLE SELF-REPAIRING EPOXY RESIN AND PREPARATION AND RECOVERY REMOULDING METHOD THEREFOR

This application is the National Stage Application of PCT/CN2018/077462, filed on Feb. 27, 2018, which is incorporated by reference for all purposes as if fully set forth herein.

TECHNICAL FIELD

This invention relates to a thermosetting resin and its preparation method. In a particular aspect, the invention relates to a self-healable epoxy resin and its preparation, recycling and remolding method. It belongs to technical field of polymer materials.

BACKGROUND OF THE INVENTION

The developing tendency of miniaturization, high frequency, high speed and fast update of electronic devices has strictly asked for better reliability and recyclability of packaging resins. The traditional method to realize better reliability is improving thermal stability and mechanical properties of resins, which is however not effective in terms of repairing microcracks or scratches caused by friction and collision.

On the other hand, the fast updating of electronic devices has brought 20-50 million tons of global electronic waste annually. However, it is well known that at present, the degradation and recycling of thermosetting resins are very expensive and consume great energy due to the permanent three-dimensional crosslinked network, and then this also blocks the recovery and recycling of noble metals and silicons in electronic devices. Therefore, it is of great importance and meaningful to achieve fast recovery and recycling of packaging epoxy resins with low energy consumption.

In recent years, intrinsic self-healable materials have attracted worldwide attention because they can repeatedly repair physical damages and flaws, prevent materials from failure and extend the service life. Therefore, to get ability of self-healing, recycling and remoldability, most self-healable epoxy resins reported have low $T_g$ values (<70° C.) and initial decomposition temperature ($T_{di}$, <300° C.). Although the relatively low $T_g$ is beneficial to realize self-healing ability and remoldability at certain temperature (from R.T. to 200° C.), the poor thermal resistance of these self-healable epoxy resins could not be used to package electric devices with high frequency, high speed and high density.

Compared to supramolecular interactions, self-healable materials dynamically crosslinked by reversible covalent bonds not only have bigger advantage to guarantee their mechanical strength, dimensional stability and thermal resistance, but also are beneficial to develop tough and heat-resistant materials with self-healing ability and remoldability.

Disulfide segments have been utilized to prepare many soft and elastic self-healable matters. The introduction of disulfide could also endow epoxy resins with self-healing ability and remoldability, but the chemical recycling through exchange reaction with small-molecular thiols or disulfides usually needs high temperature or long time; this circumstance does not fit the tendency of fast recycling with low-energy consumption of resins.

Therefore, it is still an interesting issue with great challenge to develop novel self-healable epoxy resins with superior mechanical strength, high thermal resistance, fast recyclability and remoldability for electronic packaging.

Technical Problem

Solution

Technical Solutions

In order to overcome the disadvantages of technology on existing epoxy resins, this invention provides a new self-healable epoxy resins and its preparation, recycling and remolding method. The self-healing and remolding process require low temperature and short time, which could meet the tendency of fast recycling and remolding of packaging resins with low energy consumption.

In order to achieve above purpose, the technical solution adopted by this invention is providing a method of preparing a self-healable epoxy resin, which is composed of following steps:

(1) By mass, at 20 to 30° C., 120 parts of 2-mercaptoacetic acid, 500 to 700 parts of ester solvent and 0.6 to 1.2 parts of potassium iodide were mixed homogeneously to obtain a solution; 80 to 90 parts of 30 wt % $H_2O_2$ were added dropwise to the solution and continued to react for 2 to 4 h to get 2,2'-dithiodiacetic acid;

(2) By mass, at 20 to 30° C., 100 parts of 2,2'-dithiodiacetic acid and 120 to 150 parts of anhydride were mixed homogeneously and continued to react for 2 to 4 h to get 1,4,5-oxadithiepane-2,7-dione;

(3) By mass, at 50 to 70° C., 100 parts of epoxy resin, 42 to 84 parts of 1,4,5-oxadithiepane-2,7-dione and 0 to 43 parts of methylhexahydrophthalic anhydride were mixed homogeneously. After curing, the self-healable epoxy resin was obtained.

This invention provides the method of preparing 1,4,5-oxadithiepane-2,7-dione, which is composed of following steps:

(1) By mass, at 20 to 30° C., 120 parts of 2-mercaptoacetic acid, 500 to 700 parts of ester solvent and 0.6 to 1.2 parts of potassium iodide were mixed homogeneously to obtain a solution; 80 to 90 parts of 30 wt % $H_2O_2$ were added dropwise to the solution and continued to react for 2 to 4 h to get 2,2'-dithiodiacetic acid;

(2) By mass, at 20 to 30° C., 100 parts of 2,2'-dithiodiacetic acid and 120 to 150 parts of anhydride were mixed homogeneously and continued to react for 2 to 4 h to get 1,4,5-oxadithiepane-2,7-dione.

The ester solvent described in above-mentioned technical solution is methyl acetate, ethyl acetate, propyl acetate, methyl propionate, ethyl propionate, or any combination thereof. The anhydride described in above-mentioned technical solution is acetic anhydride, trifluoroacetic anhydride, or any combination thereof.

The epoxy resin describe in above-mentioned technical solution is glycidyl ether type epoxy resin, glycidyl ester type epoxy resin, glycidyl amine type epoxy resin, aliphatic epoxides, alicyclic epoxides, or any combination thereof.

The self-healable epoxy resins and 1,4,5-oxadithiepane-2,7-dione prepared by the above-mentioned preparation method.

This invention provides the application of above-mentioned 1,4,5-oxadithiepane-2,7-dione in preparation of self-healable epoxy resins.

This invention provides the self-healing method of a kind of damaged self-healable epoxy resins, which is composed of following steps: fractured surfaces of damaged self-healable epoxy resins were brought into contact, held tightly by clamps and maintained at 160 to 200° C. for 1 to 3 h to fulfill their self-healing process. The preferred damage is fracture.

This invention provides the recycling and remolding method of a kind of self-healable epoxy resins, which is composed of following steps: ground self-healable epoxy resins were hot pressed at 160 to 200° C. for 1 to 3 h to fulfill their recycling and remolding process.

This invention provides a kind of recyclable and remoldable epoxy resins, which is composed of following steps: ground self-healable epoxy resins were hot pressed at 160 to 200° C. for 1 to 3 h to get recyclable and remoldable epoxy resins.

The Beneficial Effects of the Invention

Beneficial Effects

Compared with the existed technical solutions, this invention achieves following beneficial effects:

1. Through controlling dynamic and permanent three-dimensional crosslinked network by adjusting the weight ratio of 1,4,5-oxadithiepane-2,7-dione and methylhexahydrophthalic anhydride, the self-healable epoxy resins provided in this invention exhibit high thermal resistance ($T_g$>110° C., $T_{di}$>300° C.) as well as excellent self-healing ability, recyclability and remoldability.

2. The activation energy of disulfide is low enough to facilitate swift exchange reaction under moderate condition. Hence, the healing efficiency of self-healable epoxy resins provided in this invention is above 95% after self-healing process is fulfilled at 160° C. for 1 h.

3. Compared with existed technical solutions, the recycling and remolding method of self-healable epoxy resins provided in this invention require low temperature and short time (160° C., 1 h), which could reduce energy consumption and meet the sustainable requirement of energy saving and environmental protection. The dynamic feature of disulfide can bring energy dissipation process to improve the toughness of self-healable epoxy resins provided in this invention and reduce the generation of microcracks.

EXAMPLES OF THE INVENTION

Example 1

1) Synthesis of 2,2'-dithiodiacetic acid

Figure 1:
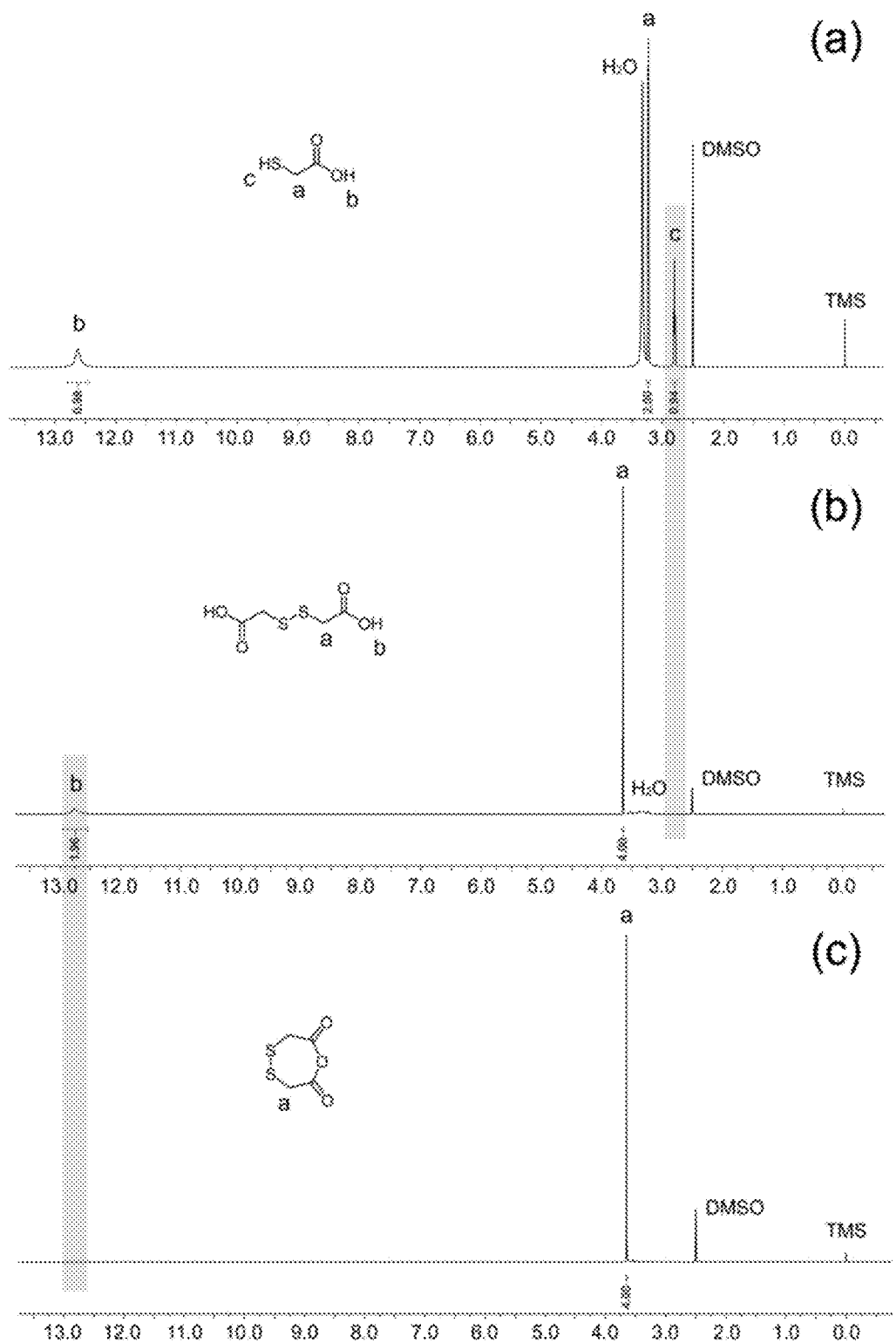
FIG. 1 is $^1$H-NMR spectra of 2,2'-dithiodiacetic acid and 1,4,5-oxadithiepane-2,7-dione synthesized in Example 1 of this invention.

By mass, at 20° C., 120 g 2-mercaptoacetic acid, 500 g ethyl acetate and 0.6 g potassium iodide were mixed homogeneously to obtain a solution A; 80 g 30 wt % $H_2O_2$ were added dropwise to solution A and continued to react for 2 h. The obtained solution was washed with 300 mL saturate $Na_2SO_3$ aqueous solution and ethyl acetate was removed under reduced pressure to get 2,2'-dithiodiacetic acid. The $^1$H-NMR spectrum of 2,2'-dithiodiacetic acid is shown in FIG. 1.

2) Synthesis of 1,4,5-oxadithiepane-2,7-dione

Figure 2:
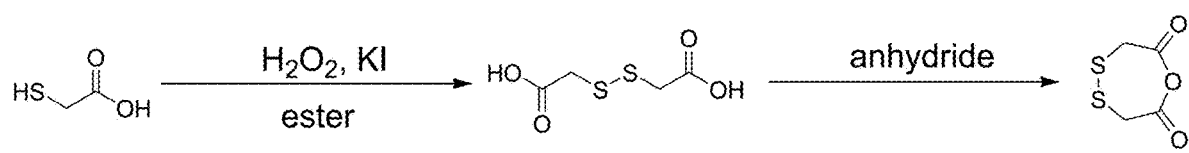
FIG. 2 is synthetic route of 1,4,5-oxadithiepane-2,7-dione synthesized in Example 1 of this invention.

By mass, at 20° C., 100 g 2,2'-dithiodiacetic acid and 150 g trifluoroacetic anhydride were mixed homogeneously and continued to react for 2 h. Excess trifluoroacetic anhydride and generated trifluoroacetic acid were removed under reduced pressure to get 1,4,5-oxadithiepane-2,7-dione. The $^1$H-NMR spectrum and synthetic route of 1,4,5-oxadithiepane-2,7-dione are shown in FIG. 1 and FIG. 2.

3) Synthesis of Self-Healable Epoxy Resins

By mass, at 50° C., 100 g glycidyl ether type epoxy resin (E51, epoxide equivalent weight of 196 g/eq), 42 g of 1,4,5-oxadithiepane-2,7-dione, 43 g methylhexahydrophthalic anhydride and 0.5 g 2-ethyl-4-methylimidazole were mixed homogeneously. After cured by the protocol of 80° C./2 h, 100° C./2 h, 120° C./2 h, 140° C./2 h and 160° C./4 h, a kind of self-healable epoxy resins was obtained. The FTIR spectrum, fracture toughness, DMA curves and TGA curve of self-healable epoxy resins are shown in FIG. 3, FIG. 4, FIG. 5 and FIG. 6.

Control Example 1 Synthesis of Conventional Epoxy Resins

By mass, at 50° C., 100 g glycidyl ether type epoxy resin (E51, epoxide equivalent weight of 196 g/eq), 86 g methylhexahydrophthalic anhydride and 0.5 g 2-ethyl-4-methylimidazole were mixed homogeneously. After cured by the protocol of 80° C./2 h, 100° C./2 h, 120° C./2 h, 140° C./2 h and 160° C./4 h, conventional epoxy resin was obtained.

The fractured surfaces of damaged conventional epoxy resin were brought into contact, held tightly by clamps and maintained at 160° C. for 1 h to fulfill self-healing process.

The FTIR spectrum, fracture toughness, DMA curves, TGA curve and digital images of self-healing process of conventional epoxy resin are shown in FIG. 3, FIG. 4, FIG. 5, FIG. 6 and FIG. 7.

FIG. 1 gives $^1$H-NMR spectra of 2,2'-dithiodiacetic acid and 1,4,5-oxadithiepane-2,7-dione prepared in Example 1. Compared with $^1$H-NMR spectra of 2-mercaptoacetic acid, the proton resonating at 2.78 ppm (c) for mercapto groups is not found in the spectrum of 2,2'-dithiodiacetic acid, indicating the formation of disulfides from thiols by oxidative $H_2O_2$. After the dehydrated condensation, no carboxylic protons at 12.75 ppm (b) are observed in spectrum of 1,4,5-oxadithiepane-2,7-dione, proving the formation of anhydrides from carboxyl groups of 2,2'-dithiodiacetic acid.

FIG. 2 gives synthetic route of 1,4,5-oxadithiepane-2,7-dione prepared in Example 1. The first step is oxidation reaction of thiols to form dynamic disulfide bonds. The second step is dehydrated condensation of carboxyl groups to form anhydrides that can be cured with epoxides.

Figure 3:
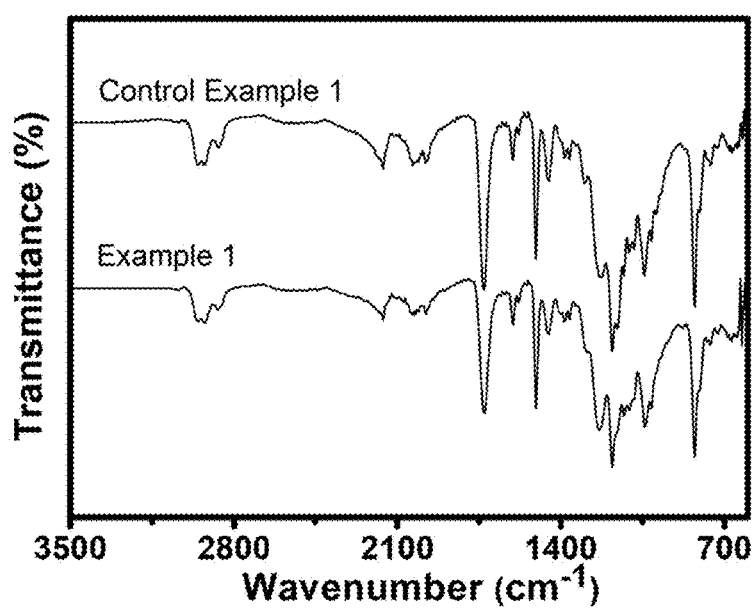
FIG. 3 is FTIR spectra of self-healable epoxy resin synthesized in Example 1 and conventional epoxy resin synthesized in Control Example 1 of this invention.

FIG. 3 gives FTIR spectra of self-healable epoxy resin prepared in Example 1 and conventional epoxy resin prepared in Control Example 1. The characteristic vibration between 3000 and 2800 cm$^{-1}$ represent methyl groups (2960 cm$^{-1}$ and 2870 cm$^{-1}$) and methylene groups (2920 cm$^{-1}$ and 2850 cm$^{-1}$). The strong stretching vibration at 1730 cm$^{-1}$ is attributed to carbonyl groups in esters induced by the reaction between epoxides and anhydrides. The appearance of C—S vibration at 1412 cm$^{-1}$ indicates the successful introduction of disulfide groups in the crosslinked network. No obvious asymmetrical stretching vibration peaks assigned to epoxide groups (910 and 845 cm$^{-1}$) are found, so epoxides of self-healable epoxy resin prepared in Example 1 and conventional epoxy resin prepared in Control Example 1 have thoroughly reacted with hardeners.

Figure 4:
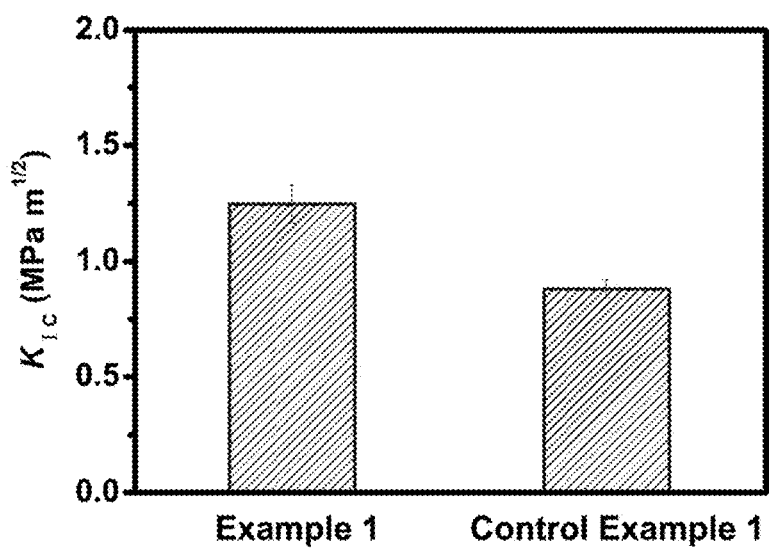
FIG. 4 is fracture toughness of self-healable epoxy resin synthesized in Example 1 and conventional epoxy resin synthesized in Control Example 1 of this invention.

FIG. 4 gives fracture toughness of self-healable epoxy resin prepared in Example 1 and conventional epoxy resin prepared in Control Example 1. The dynamic disulfide bonds in 1,4,5-oxadithiepane-2,7-dione can provide unique energy dissipation process to improve fracture toughness. Hence, the $K_{IC}$ of self-healable epoxy resin prepared in Example 1 is 1.25±0.08 MPa m$^{1/2}$, which is higher than that of conventional epoxy resin (0.88±0.04 MPa m$^{1/2}$) prepared in Control Example 1.

Figure 5:
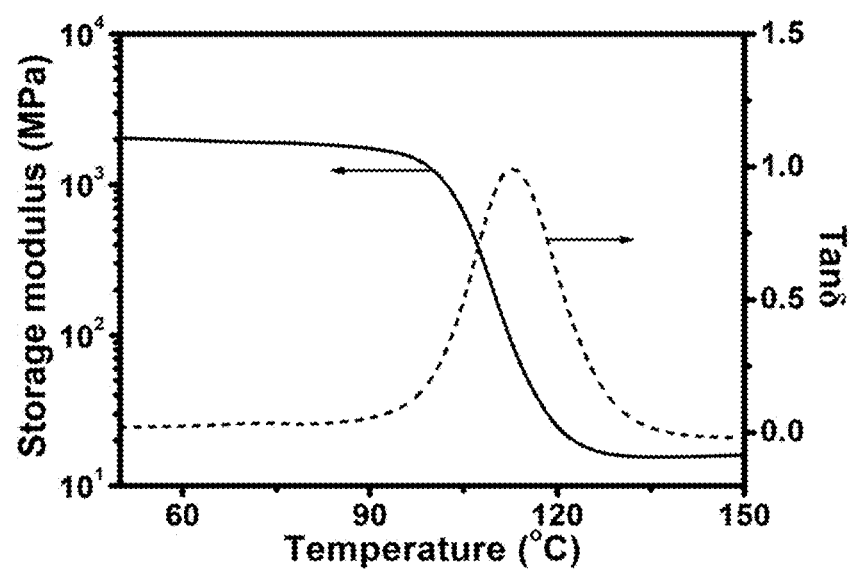
FIG. 5 is DMA curves of self-healable epoxy resin synthesized in Example 1 of this invention.

FIG. 5 gives DMA curves of self-healable epoxy resin prepared in Example 1. The curve shows a single symmetrical pattern, so the peak temperature of tan δ-temperature curve is considered as $T_g$. The cyclohexyl in methylhexahydrophthalic anhydride has greater rigidity than flexible chain in 1,4,5-oxadithiepane-2,7-dione, so the $T_g$ of self-healable epoxy resin prepared in Example 1 is 113° C. that is higher than existed technical solutions (<70° C.).

Figure 6:
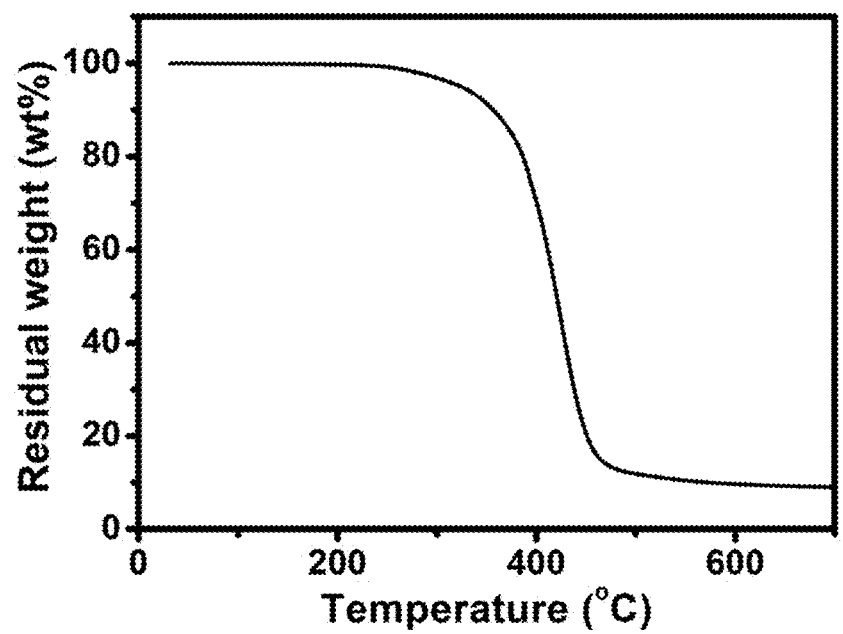
FIG. 6 is TGA curve of self-healable epoxy resin synthesized in Example 1 of this invention.

FIG. 6 gives TGA curve of self-healable epoxy resin prepared in Example 1. $T_{di}$ is mainly dependent on the decomposition temperature of the weakest bond in a material, while the bonding energy of dynamic disulfide bonds in 1,4,5-oxadithiepane-2,7-dione is less stable than that of aliphatic and alicyclic chains in methylhexahydrophthalic anhydride, so the $T_{di}$ of self-healable epoxy resin prepared in Example 1 is 324° C. This is a common problem for current self-healable materials based on reversible covalent bonds, but the value is still higher than existed technical solutions $T_{di}$<300° C.).

Example 2

1) Synthesis of 2,2'-dithiodiacetic acid
By mass, at 25° C., 120 g 2-mercaptoacetic acid, 600 g methyl acetate and 0.8 g potassium iodide were mixed homogeneously to obtain a solution A; 85 g 30 wt % $H_2O_2$ were added dropwise to solution A and continued to react for 3 h. The obtained solution was washed with 300 mL saturate $Na_2SO_3$ aqueous solution and methyl acetate was removed under reduced pressure to get 2,2'-dithiodiacetic acid.

2) Synthesis of 1,4,5-oxadithiepane-2,7-dione
By mass, at 25° C., 100 g 2,2'-dithiodiacetic acid and 135 g acetic anhydride were mixed homogeneously and continued to react for 3 h. Excess acetic anhydride and generated acetic acid were removed under reduced pressure to get 1,4,5-oxadithiepane-2,7-dione.

3) Synthesis of Self-Healable Epoxy Resins
By mass, at 60° C., 100 g glycidyl ester type epoxy resin (672, epoxide equivalent weight of 161 g/eq), 52 g of 1,4,5-oxadithiepane-2,7-dione, 32 g methylhexahydrophthalic anhydride and 0.5 g 2-ethyl-4-methylimidazole were mixed homogeneously. After cured by the protocol of 80° C./2 h, 100° C./2 h, 120° C./2 h, 140° C./2 h and 160° C./4 h, a kind of self-healable epoxy resins was obtained. $T_g$>110° C. $T_{di}$>300° C., the fracture toughness is better.

4) Self-Healing Method of Self-Healable Epoxy Resins
Fractured surfaces of damaged self-healable epoxy resins were brought into contact, held tightly by clamps, and maintained at 180° C. for 2 h. After self-healing process, the healing efficiency is above 95%. No peeling off happened along the interface of the healed samples under tensile lap shear, indicating the overlapped sections have fused together as entirety via the exchange reaction between dynamic disulfide bonds.

5) Recycling and Remolding Method of Self-Healable Epoxy Resins
Ground self-healable epoxy resins were hot pressed at 180° C. for 2 h to get recyclable and remoldable epoxy resins. The obtained square panel has no observable cracks, clearly demonstrating that ground self-healable epoxy resin powders have been bonded together through the topology rearrangement based on the exchangeable feature of dynamic disulfide linkages. This result provides a clear evidence of good self-healing ability, recyclability and remoldability for self-healable epoxy resins prepared in this invention.

Example 3

1) Synthesis of 2,2'-dithiodiacetic acid
By mass, at 30° C., 120 g 2-mercaptoacetic acid, 700 g propyl acetate and 1.0 g potassium iodide were mixed homogeneously to obtain a solution A; 90 g 30 wt % $H_2O_2$ were added dropwise to solution A and continued to react for 4 h. The obtained solution was washed with 300 mL saturate $Na_2SO_3$ aqueous solution and propyl acetate was removed under reduced pressure to get 2,2'-dithiodiacetic acid.

2) Synthesis of 1,4,5-oxadithiepane-2,7-dione
By mass, at 30° C., 100 g 2,2'-dithiodiacetic acid and 120 g acetic anhydride were mixed homogeneously and continued to react for 4 h. Excess acetic anhydride and generated acetic acid were removed under reduced pressure to get 1,4,5-oxadithiepane-2,7-dione.

3) Synthesis of Self-Healable Epoxy Resins
By mass, at 70° C., 100 g glycidyl amine type epoxy resin (AFG-90, epoxide equivalent weight of 118 g/eq), 60 g of 1,4,5-oxadithiepane-2,7-dione, 25 g methylhexahydrophthalic anhydride and 0.5 g 2-ethyl-4-methylimidazole were mixed homogeneously. After cured by the protocol of 80° C./2 h, 100° C./2 h, 120° C./2 h, 140° C./2 h and 160° C./4 h, a kind of self-healable epoxy resins was obtained. $T_g$>110° C. $T_{di}$>300° C., the fracture toughness is better.

4) Self-Healing Method of Self-Healable Epoxy Resins
Fractured surfaces of damaged self-healable epoxy resins were brought into contact, held tightly by clamps, and maintained at 200° C. for 3 h. After self-healing process, the healing efficiency is above 95%. No peeling off happened along the interface of the healed samples under tensile lap shear, indicating the overlapped sections have fused together as entirety via the exchange reaction between dynamic disulfide bonds.

5) Recycling and Remolding Method of Self-Healable Epoxy Resins Ground self-healable epoxy resins were hot pressed at 200° C. for 3 h to get recyclable and remoldable epoxy resins. The obtained square panel has no observable cracks, clearly demonstrating that ground self-healable epoxy resin powders have been bonded together through the topology rearrangement based on the exchangeable feature of dynamic disulfide linkages. This result provides a clear evidence of good self-healing ability, recyclability and remoldability for self-healable epoxy resins prepared in this invention.

Example 4

1) Synthesis of 2,2'-dithiodiacetic acid

By mass, at 25° C., 120 g 2-mercaptoacetic acid, 500 g methyl propionate and 1.2 g potassium iodide were mixed homogeneously to obtain a solution A; 85 g 30 wt % $H_2O_2$ were added dropwise to solution A and continued to react for 2.5 h. The obtained solution was washed with 300 mL saturate $Na_2SO_3$ aqueous solution and methyl propionate was removed under reduced pressure to get 2,2'-dithiodiacetic acid.

2) Synthesis of 1,4,5-oxadithiepane-2,7-dione

By mass, at 25° C., 100 g 2,2'-dithiodiacetic acid, 75 g acetic anhydride and 75 g trifluoroacetic anhydride were mixed homogeneously and continued to react for 2.5 h. Excess anhydride and generated carboxylic acid were removed under reduced pressure to get 1,4,5-oxadithiepane-2,7-dione.

3) Synthesis of Self-Healable Epoxy Resins

By mass, at 65° C., 100 g aliphatic epoxides (EPG-205, epoxide equivalent weight of 178 g/eq), 44 g of 1,4,5-oxadithiepane-2,7-dione, 42 g methylhexahydrophthalic anhydride and 0.5 g 2-ethyl-4-methylimidazole were mixed homogeneously. After cured by the protocol of 80° C./2 h, 100° C./2 h, 120° C./2 h, 140° C./2 h and 160° C./4 h, a kind of self-healable epoxy resins was obtained. $T_g$>110° C. $T_{di}$>300° C., the fracture toughness is better.

4) Self-Healing Method of Self-Healable Epoxy Resins

Fractured surfaces of damaged self-healable epoxy resins were brought into contact, held tightly by clamps, and maintained at 160° C. for 3 h. After self-healing process, the healing efficiency is above 95%. No peeling off happened along the interface of the healed samples under tensile lap shear, indicating the overlapped sections have fused together as entirety via the exchange reaction between dynamic disulfide bonds.

5) Recycling and Remolding Method of Self-Healable Epoxy Resins

Ground self-healable epoxy resins were hot pressed at 185° C. for 2 h to get recyclable and remoldable epoxy resins. The obtained square panel has no observable cracks, clearly demonstrating that ground self-healable epoxy resin powders have been bonded together through the topology rearrangement based on the exchangeable feature of dynamic disulfide linkages. This result provides a clear evidence of good self-healing ability, recyclability and remoldability for self-healable epoxy resins prepared in this invention.

Example 5

1) Synthesis of 2,2'-dithiodiacetic acid

By mass, at 25° C., 120 g 2-mercaptoacetic acid, 600 g ethyl propionate and 0.7 g potassium iodide were mixed homogeneously to obtain a solution A; 85 g 30 wt % $H_2O_2$ were added dropwise to solution A and continued to react for 2 h. The obtained solution was washed with 300 mL saturate $Na_2SO_3$ aqueous solution and ethyl propionate was removed under reduced pressure to get 2,2'-dithiodiacetic acid.

2) Synthesis of 1,4,5-oxadithiepane-2,7-dione

By mass, at 25° C., 100 g 2,2'-dithiodiacetic acid and 150 g trifluoroacetic anhydride were mixed homogeneously and continued to react for 2 h. Excess trifluoroacetic anhydride and generated trifluoroacetic acid were removed under reduced pressure to get 1,4,5-oxadithiepane-2,7-dione.

3) Synthesis of Self-Healable Epoxy Resins

By mass, at 50° C., 100 g alicyclic epoxides (H71, epoxide equivalent weight of 154 g/eq), 45 g of 1,4,5-oxadithiepane-2,7-dione, 41 g methylhexahydrophthalic anhydride and 0.5 g 2-ethyl-4-methylimidazole were mixed homogeneously. After cured by the protocol of 80° C./2 h, 100° C./2 h, 120° C./2 h, 140° C./2 h and 160° C./4 h, a kind of self-healable epoxy resins was obtained. $T_g$>110° C. $T_{di}$>300° C., the fracture toughness is better.

4) Self-Healing Method of Self-Healable Epoxy Resins

Fractured surfaces of damaged self-healable epoxy resins were brought into contact, held tightly by clamps, and maintained at 160° C. for 2 h. After self-healing process, the healing efficiency is above 95%. No peeling off happened along the interface of the healed samples under tensile lap shear, indicating the overlapped sections have fused together as entirety via the exchange reaction between dynamic disulfide bonds.

5) Recycling and Remolding Method of Self-Healable Epoxy Resins

Ground self-healable epoxy resins were hot pressed at 160° C. for 3 h to get recyclable and remoldable epoxy resins. The obtained square panel has no observable cracks, clearly demonstrating that ground self-healable epoxy resin powders have been bonded together through the topology rearrangement based on the exchangeable feature of dynamic disulfide linkages. This result provides a clear evidence of good self-healing ability, recyclability and remoldability for self-healable epoxy resins prepared in this invention.

Example 6

1) Synthesis of 2,2'-dithiodiacetic acid

By mass, at 23° C., 120 g 2-mercaptoacetic acid, 250 g ethyl acetate, 250 g propyl acetate and 0.6 g potassium iodide were mixed homogeneously to obtain a solution A; 83 g 30 wt % $H_2O_2$ were added dropwise to solution A and continued to react for 3 h. The obtained solution was washed with 300 mL saturate $Na_2SO_3$ aqueous solution and ethyl acetate and propyl acetate were removed under reduced pressure to get 2,2'-dithiodiacetic acid.

2) Synthesis of 1,4,5-oxadithiepane-2,7-dione

By mass, at 23° C., 100 g 2,2'-dithiodiacetic acid and 140 g trifluoroacetic anhydride were mixed homogeneously and continued to react for 2 h. Excess trifluoroacetic anhydride and generated trifluoroacetic acid were removed under reduced pressure to get 1,4,5-oxadithiepane-2,7-dione.

3) Synthesis of Self-Healable Epoxy Resins

By mass, at 50° C., 100 g glycidyl ether type epoxy resin (E51, epoxide equivalent weight of 196 g/eq), 62 g of 1,4,5-oxadithiepane-2,7-dione, 24 g methylhexahydrophthalic anhydride and 0.5 g 2-ethyl-4-methylimidazole were mixed homogeneously. After cured by the protocol of 80°

C./2 h, 100° C./2 h, 120° C./2 h, 140° C./2 h and 160° C./4 h, a kind of self-healable epoxy resins was obtained. $T_g$>110° C. $T_{di}$>300° C., the fracture toughness is better.

4) Self-Healing Method of Self-Healable Epoxy Resins

Fractured surfaces of damaged self-healable epoxy resins were brought into contact, held tightly by clamps, and maintained at 160° C. for 2 h. After self-healing process, the healing efficiency is above 95%. No peeling off happened along the interface of the healed samples under tensile lap shear, indicating the overlapped sections have fused together as entirety via the exchange reaction between dynamic disulfide bonds.

5) Recycling and Remolding Method of Self-Healable Epoxy Resins

Ground self-healable epoxy resins were hot pressed at 160° C. for 3 h to get recyclable and remoldable epoxy resins. The obtained square panel has no observable cracks, clearly demonstrating that ground self-healable epoxy resin powders have been bonded together through the topology rearrangement based on the exchangeable feature of dynamic disulfide linkages. This result provides a clear evidence of good self-healing ability, recyclability and remoldability for self-healable epoxy resins prepared in this invention.

Example 7

1) Synthesis of 2,2'-dithiodiacetic acid

By mass, at 25° C., 120 g 2-mercaptoacetic acid, 250 g methyl acetate, 350 g methyl propionate and 1.1 g potassium iodide were mixed homogeneously to obtain a solution A; 84 g 30 wt % $H_2O_2$ were added dropwise to solution A and continued to react for 2 h. The obtained solution was washed with 300 mL saturate $Na_2SO_3$ aqueous solution and methyl acetate and methyl propionate were removed under reduced pressure to get 2,2'-dithiodiacetic acid.

2) Synthesis of 1,4,5-oxadithiepane-2,7-dione

By mass, at 22° C., 100 g 2,2'-dithiodiacetic acid and 150 g trifluoroacetic anhydride were mixed homogeneously and continued to react for 2 h. Excess trifluoroacetic anhydride and generated trifluoroacetic acid were removed under reduced pressure to get 1,4,5-oxadithiepane-2,7-dione.

3) Synthesis of Self-Healable Epoxy Resins

By mass, at 50° C., 100 g alicyclic epoxides (H71, epoxide equivalent weight of 154 g/eq), 70 g of 1,4,5-oxadithiepane-2,7-dione, 14 g methylhexahydrophthalic anhydride and 0.5 g 2-ethyl-4-methylimidazole were mixed homogeneously. After cured by the protocol of 80° C./2 h, 100° C./2 h, 120° C./2 h, 140° C./2 h and 160° C./4 h, a kind of self-healable epoxy resins was obtained. $T_g$>110° C. $T_{di}$>300° C., the fracture toughness is better.

4) Self-Healing Method of Self-Healable Epoxy Resins

Fractured surfaces of damaged self-healable epoxy resins were brought into contact, held tightly by clamps, and maintained at 170° C. for 1.5 h. After self-healing process, the healing efficiency is above 95%. No peeling off happened along the interface of the healed samples under tensile lap shear, indicating the overlapped sections have fused together as entirety via the exchange reaction between dynamic disulfide bonds.

5) Recycling and Remolding Method of Self-Healable Epoxy Resins Ground self-healable epoxy resins were hot pressed at 170° C. for 1.5 h to get recyclable and remoldable epoxy resins. The obtained square panel has no observable cracks, clearly demonstrating that ground self-healable epoxy resin powders have been bonded together through the topology rearrangement based on the exchangeable feature of dynamic disulfide linkages. This result provides a clear evidence of good self-healing ability, recyclability and remoldability for self-healable epoxy resins prepared in this invention.

Example 8

1) Synthesis of 2,2'-dithiodiacetic acid By mass, at 25° C., 120 g 2-mercaptoacetic acid, 300 g ethyl acetate, 300 g ethyl propionate and 1.0 g potassium iodide were mixed homogeneously to obtain a solution A; 85 g 30 wt % $H_2O_2$ were added dropwise to solution A and continued to react for 2.5 h. The obtained solution was washed with 300 mL saturate $Na_2SO_3$ aqueous solution and ethyl acetate and ethyl propionate were removed under reduced pressure to get 2,2'-dithiodiacetic acid.

2) Synthesis of 1,4,5-oxadithiepane-2,7-dione By mass, at 24° C., 100 g 2,2'-dithiodiacetic acid and 135 g trifluoroacetic anhydride were mixed homogeneously and continued to react for 2 h. Excess trifluoroacetic anhydride and generated trifluoroacetic acid were removed under reduced pressure to get 1,4,5-oxadithiepane-2,7-dione.

3) Synthesis of Self-Healable Epoxy Resins By mass, at 55° C., 100 g glycidyl ether type epoxy resin (E51, epoxide equivalent weight of 196 g/eq), 52 g of 1,4,5-oxadithiepane-2,7-dione, 33 g methylhexahydrophthalic anhydride and 0.5 g 2-ethyl-4-methylimidazole were mixed homogeneously. After cured by the protocol of 80° C./2 h, 100° C./2 h, 120° C./2 h, 140° C./2 h and 160° C./4 h, a kind of self-healable epoxy resins was obtained. $T_g$>110° C. $T_{di}$>300° C., the fracture toughness is better.

4) Self-Healing Method of Self-Healable Epoxy Resins

Fractured surfaces of damaged self-healable epoxy resins were brought into contact, held tightly by clamps, and maintained at 160° C. for 1.5 h. After self-healing process, the healing efficiency is above 95%. No peeling off happened along the interface of the healed samples under tensile lap shear, indicating the overlapped sections have fused together as entirety via the exchange reaction between dynamic disulfide bonds.

5) Recycling and Remolding Method of Self-Healable Epoxy Resins

Ground self-healable epoxy resins were hot pressed at 160° C. for 1.5 h to get recyclable and remoldable epoxy resins. The obtained square panel has no observable cracks, clearly demonstrating that ground self-healable epoxy resin powders have been bonded together through the topology rearrangement based on the exchangeable feature of dynamic disulfide linkages. This result provides a clear evidence of good self-healing ability, recyclability and remoldability for self-healable epoxy resins prepared in this invention.

Example 9

1) Synthesis of 2,2'-dithiodiacetic acid

By mass, at 25° C., 120 g 2-mercaptoacetic acid, 600 g ethyl acetate and 0.6 g potassium iodide were mixed homogeneously to obtain a solution A; 80 g 30 wt % $H_2O_2$ were added dropwise to solution A and continued to react for 2 h. The obtained solution was washed with 300 mL saturate $Na_2SO_3$ aqueous solution and ethyl acetate was removed under reduced pressure to get 2,2'-dithiodiacetic acid.

2) Synthesis of 1,4,5-oxadithiepane-2,7-dione

By mass, at 24° C., 100 g 2,2'-dithiodiacetic acid and 140 g trifluoroacetic anhydride were mixed homogeneously and continued to react for 2 h. Excess trifluoroacetic anhydride and generated trifluoroacetic acid were removed under reduced pressure to get 1,4,5-oxadithiepane-2,7-dione.

3) Synthesis of Self-Healable Epoxy Resins

By mass, at 55° C., 50 g glycidyl ether type epoxy resin (E51, epoxide equivalent weight of 196 g/eq), 50 g glycidyl ester type epoxy resin (672, epoxide equivalent weight of 161 g/eq), 44 g of 1,4,5-oxadithiepane-2,7-dione, 41 g methylhexahydrophthalic anhydride and 0.5 g 2-ethyl-4-methylimidazole were mixed homogeneously. After cured by the protocol of 80° C./2 h, 100° C./2 h, 120° C./2 h, 140° C./2 h and 160° C./4 h, a kind of self-healable epoxy resins was obtained. $T_g$>110° C. $T_{di}$>300° C., the fracture toughness is better.

4) Self-Healing Method of Self-Healable Epoxy Resins

Fractured surfaces of damaged self-healable epoxy resins were brought into contact, held tightly by clamps, and maintained at 180° C. for 2.5 h. After self-healing process, the healing efficiency is above 95%. No peeling off happened along the interface of the healed samples under tensile lap shear, indicating the overlapped sections have fused together as entirety via the exchange reaction between dynamic disulfide bonds.

5) Recycling and Remolding Method of Self-Healable Epoxy Resins

Ground self-healable epoxy resins were hot pressed at 180° C. for 2.5 h to get recyclable and remoldable epoxy resins. The obtained square panel has no observable cracks, clearly demonstrating that ground self-healable epoxy resin powders have been bonded together through the topology rearrangement based on the exchangeable feature of dynamic disulfide linkages. This result provides a clear evidence of good self-healing ability, recyclability and remoldability for self-healable epoxy resins prepared in this invention.

Example 10

1) Synthesis of 2,2'-dithiodiacetic acid

By mass, at 30° C., 120 g 2-mercaptoacetic acid, 700 g ethyl acetate and 0.6 g potassium iodide were mixed homogeneously to obtain a solution A; 90 g 30 wt % $H_2O_2$ were added dropwise to solution A and continued to react for 2.5 h. The obtained solution was washed with 300 mL saturate $Na_2SO_3$ aqueous solution and ethyl acetate was removed under reduced pressure to get 2,2'-dithiodiacetic acid.

2) Synthesis of 1,4,5-oxadithiepane-2,7-dione

By mass, at 26° C., 100 g 2,2'-dithiodiacetic acid and 150 g acetic anhydride were mixed homogeneously and continued to react for 2.5 h. Excess acetic anhydride and generated acetic acid were removed under reduced pressure to get 1,4,5-oxadithiepane-2,7-dione.

3) Synthesis of Self-Healable Epoxy Resins

By mass, at 60° C., 40 g alicyclic epoxides (H71, epoxide equivalent weight of 154 g/eq), 60 g glycidyl ester type epoxy resin (672, epoxide equivalent weight of 161 g/eq), 45 g of 1,4,5-oxadithiepane-2,7-dione, 39 g methylhexahydrophthalic anhydride and 0.5 g 2-ethyl-4-methylimidazole were mixed homogeneously. After cured by the protocol of 80° C./2 h, 100° C./2 h, 120° C./2 h, 140° C./2 h and 160° C./4 h, a kind of self-healable epoxy resins was obtained. $T_g$>110° C. $T_{di}$>300° C., the fracture toughness is better.

4) Self-Healing Method of Self-Healable Epoxy Resins

Fractured surfaces of damaged self-healable epoxy resins were brought into contact, held tightly by clamps, and maintained at 175° C. for 1.5 h. After self-healing process, the healing efficiency is above 95%. No peeling off happened along the interface of the healed samples under tensile lap shear, indicating the overlapped sections have fused together as entirety via the exchange reaction between dynamic disulfide bonds.

5) Recycling and Remolding Method of Self-Healable Epoxy Resins

Ground self-healable epoxy resins were hot pressed at 175° C. for 3 h to get recyclable and remoldable epoxy resins. The obtained square panel has no observable cracks, clearly demonstrating that ground self-healable epoxy resin powders have been bonded together through the topology rearrangement based on the exchangeable feature of dynamic disulfide linkages. This result provides a clear evidence of good self-healing ability, recyclability and remoldability for self-healable epoxy resins prepared in this invention.

Example 11

1) Synthesis of 2,2'-dithiodiacetic acid

By mass, at 30° C., 120 g 2-mercaptoacetic acid, 600 g ethyl acetate and 0.8 g potassium iodide were mixed homogeneously to obtain a solution A; 90 g 30 wt % $H_2O_2$ were added dropwise to solution A and continued to react for 2.5 h. The obtained solution was washed with 300 mL saturate $Na_2SO_3$ aqueous solution and ethyl acetate was removed under reduced pressure to get 2,2'-dithiodiacetic acid.

2) Synthesis of 1,4,5-oxadithiepane-2,7-dione

By mass, at 27° C., 100 g 2,2'-dithiodiacetic acid and 150 g acetic anhydride were mixed homogeneously and continued to react for 2 h. Excess acetic anhydride and generated acetic acid were removed under reduced pressure to get 1,4,5-oxadithiepane-2,7-dione.

3) Synthesis of Self-Healable Epoxy Resins

By mass, at 70° C., 70 g alicyclic epoxides (H71, epoxide equivalent weight of 154 g/eq), 30 g glycidyl ether type epoxy resin (E51, epoxide equivalent weight of 196 g/eq), 52 g of 1,4,5-oxadithiepane-2,7-dione, 31 g methylhexahydrophthalic anhydride and 0.5 g 2-ethyl-4-methylimidazole were mixed homogeneously. After cured by the protocol of 80° C./2 h, 100° C./2 h, 120° C./2 h, 140° C./2 h and 160° C./4 h, a kind of self-healable epoxy resins was obtained. $T_g$>10° C. $T_{di}$>300° C., the fracture toughness is better.

4) Self-Healing Method of Self-Healable Epoxy Resins

Fractured surfaces of damaged self-healable epoxy resins were brought into contact, held tightly by clamps, and maintained at 175° C. for 2.5 h. After self-healing process, the healing efficiency is above 95%. No peeling off happened along the interface of the healed samples under tensile lap shear, indicating the overlapped sections have fused together as entirety via the exchange reaction between dynamic disulfide bonds.

5) Recycling and Remolding Method of Self-Healable Epoxy Resins

Ground self-healable epoxy resins were hot pressed at 175° C. for 3 h to get recyclable and remoldable epoxy resins. The obtained square panel has no observable cracks, clearly demonstrating that ground self-healable epoxy resin powders have been bonded together through the topology rearrangement based on the exchangeable feature of dynamic disulfide linkages. This result provides a clear evidence of good self-healing ability, recyclability and remoldability for self-healable epoxy resins prepared in this invention.

Example 12

1) Synthesis of 2,2'-dithiodiacetic acid

By mass, at 30° C., 120 g 2-mercaptoacetic acid, 550 g propyl acetate and 0.9 g potassium iodide were mixed homogeneously to obtain a solution A; 82 g 30 wt % $H_2O_2$ were added dropwise to solution A and continued to react for 2 h. The obtained solution was washed with 300 mL saturate $Na_2SO_3$ aqueous solution and propyl acetate was removed under reduced pressure to get 2,2'-dithiodiacetic acid.

2) Synthesis of 1,4,5-oxadithiepane-2,7-dione

By mass, at 25° C., 100 g 2,2'-dithiodiacetic acid and 145 g acetic anhydride were mixed homogeneously and continued to react for 2.5 h. Excess acetic anhydride and generated acetic acid were removed under reduced pressure to get 1,4,5-oxadithiepane-2,7-dione.

3) Synthesis of Self-Healable Epoxy Resins

By mass, at 60° C., 35 g aliphatic epoxides (EPG-205, epoxide equivalent weight of 178 g/eq), 65 g glycidyl amine type epoxy resin (AFG-90, epoxide equivalent weight of 118 g/eq), 62 g of 1,4,5-oxadithiepane-2,7-dione, 21 g methylhexahydrophthalic anhydride and 0.5 g 2-ethyl-4-methylimidazole were mixed homogeneously. After cured by the protocol of 80° C./2 h, 100° C./2 h, 120° C./2 h, 140° C./2 h and 160° C./4 h, a kind of self-healable epoxy resins was obtained. $T_g$>110° C. $T_{di}$>300° C., the fracture toughness is better.

4) Self-Healing Method of Self-Healable Epoxy Resins

Fractured surfaces of damaged self-healable epoxy resins were brought into contact, held tightly by clamps, and maintained at 185° C. for 1.5 h. After self-healing process, the healing efficiency is above 95%. No peeling off happened along the interface of the healed samples under tensile lap shear, indicating the overlapped sections have fused together as entirety via the exchange reaction between dynamic disulfide bonds.

5) Recycling and Remolding Method of Self-Healable Epoxy Resins

Ground self-healable epoxy resins were hot pressed at 175° C. for 3 h to get recyclable and remoldable epoxy resins. The obtained square panel has no observable cracks, clearly demonstrating that ground self-healable epoxy resin powders have been bonded together through the topology rearrangement based on the exchangeable feature of dynamic disulfide linkages. This result provides a clear evidence of good self-healing ability, recyclability and remoldability for self-healable epoxy resins prepared in this invention.

Example 13

Self-Healing Method of Self-Healable Epoxy Resins

Figure 7:
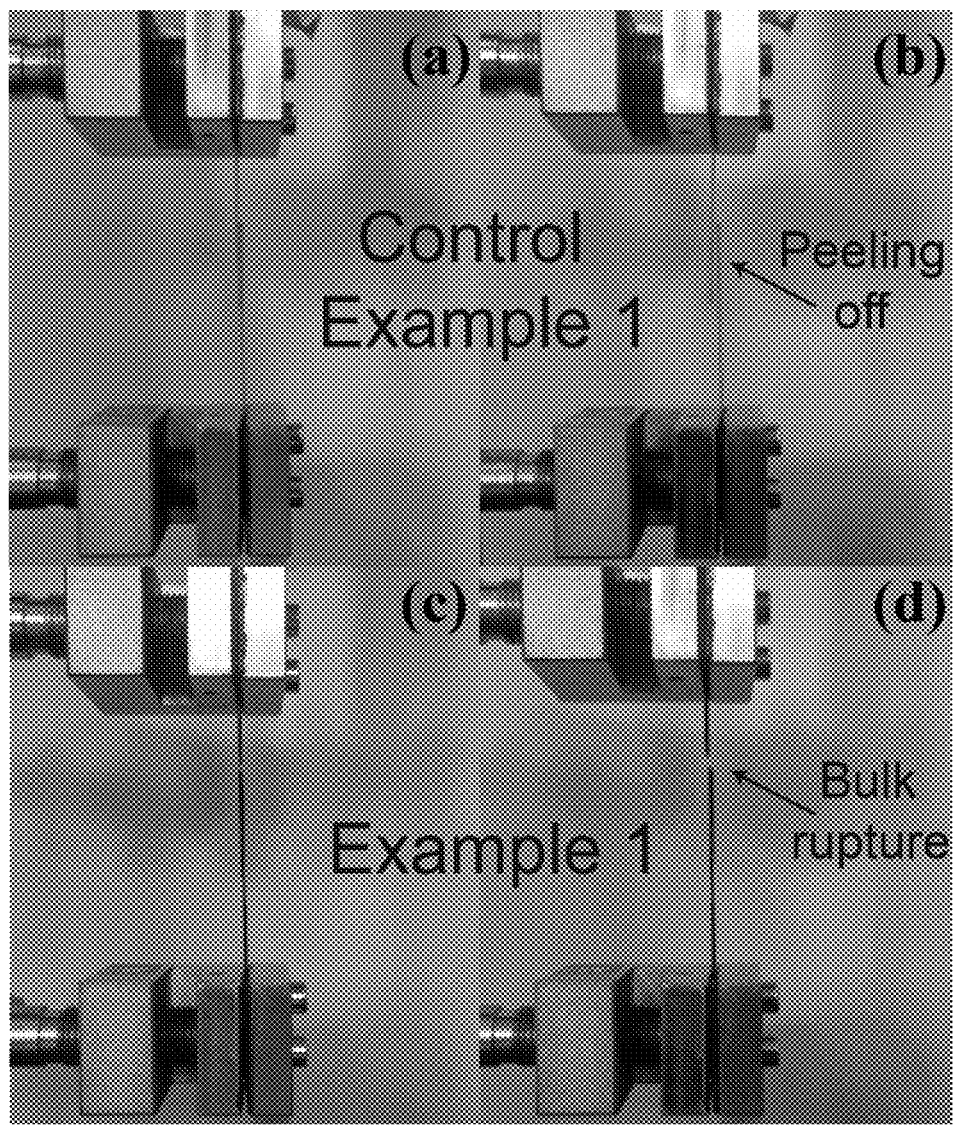
FIG. 7 is digital images of self-healing process of self-healable epoxy resin synthesized in Example 13 and conventional epoxy resin synthesized in Control Example 1 of this invention.
Figure 8:
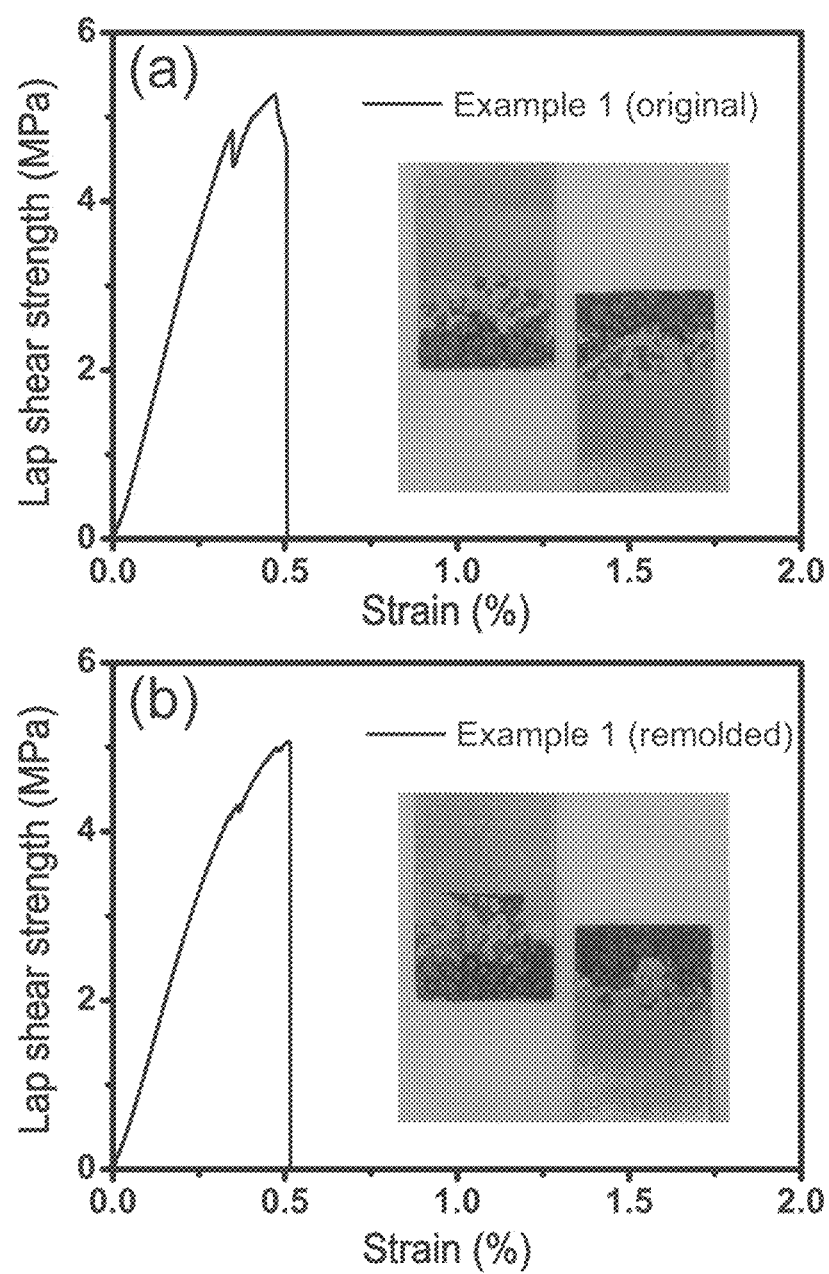
FIG. 8 is original (a) and self-healed (b) stress-strain curves and images under tensile lap shear tests of self-healable epoxy resin synthesized in Example 13 of this invention.

Fractured surfaces of damaged self-healable epoxy resins prepared in Example 1 were brought into contact, held tightly by clamps, and maintained at 160° C. for 1 h to fulfill self-healing process. The digital images of self-healing process of self-healable epoxy resins and original (a) and self-healed (b) stress-strain curves and images under tensile lap shear tests of self-healable epoxy resins are shown in FIG. 7 and FIG. 8.

Example 14

Recycling and Remolding Method of Self-Healable Epoxy Resins

Figure 10:
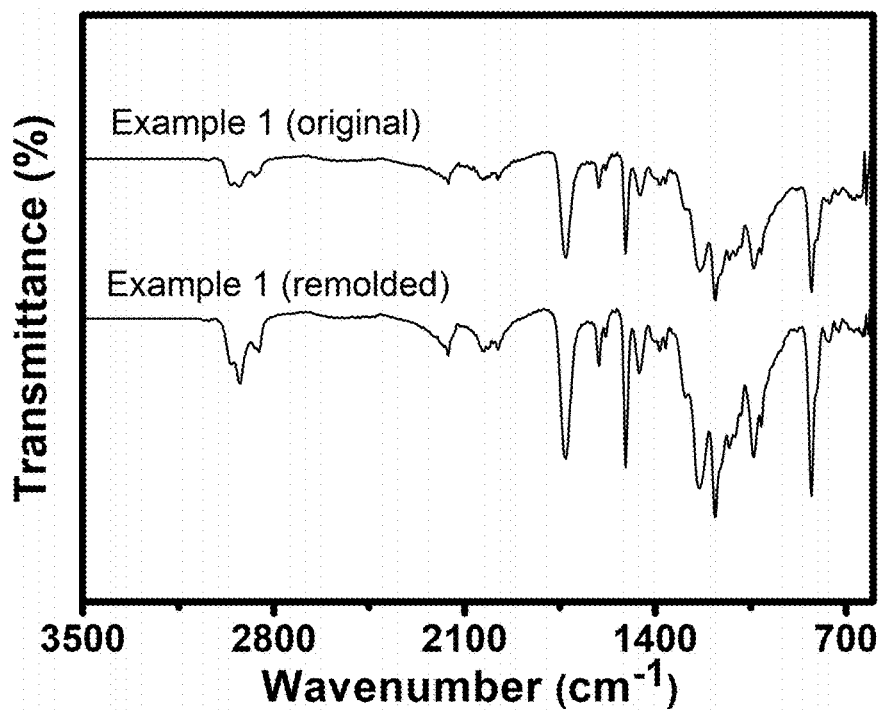
FIG. 10 is FTIR spectra of original and remolded self-healable epoxy resin synthesized in Example 14 of this invention.
Figure 11:
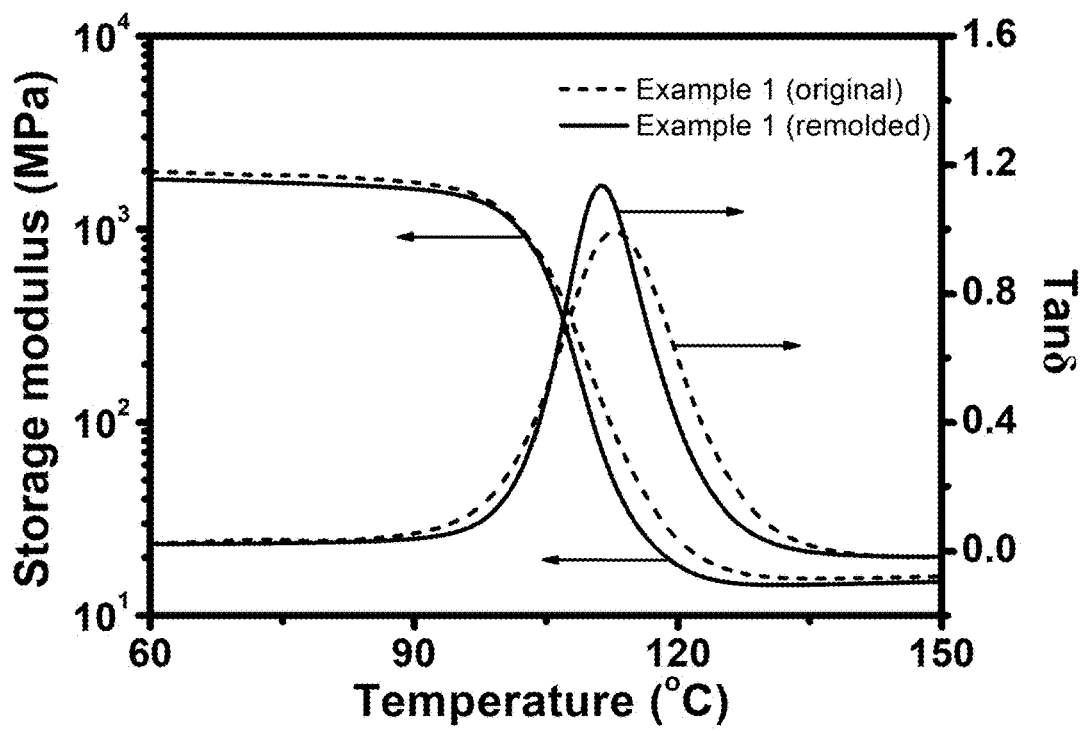
FIG. 11 is DMA curves of original and remolded self-healable epoxy resin synthesized in Example 14 of this invention.

Ground self-healable epoxy resins prepared in Example 1 were hot pressed at 160° C. for 1 h to get recyclable and remoldable epoxy resins. The digital images of recycling and remolding process, FTIR spectra and DMA curves of original and remolded self-healable epoxy resin are shown in FIG. 9, FIG. 10 and FIG. 11.

FIG. 7 gives digital images of self-healing process of self-healable epoxy resin prepared in Example 1 and conventional epoxy resin prepared in Control Example 1. Good adhesion is observed at the interface of overlapped sections of conventional epoxy resin via the segmental diffusion after heated at 160° C. for 1 h. However, peeling off takes place immediately when the samples are suffered from shear stress, demonstrating that conventional epoxy resin prepared in Control Example 1 does not have self-healing ability. Self-healable epoxy resin prepared in Example 1 shows different result under the same self-healing condition. No peeling off happens along the interface of Ep3 under tensile lap shear, and the rupture occurs in the bulk sample upon the breaking load. This phenomenon suggests that self-healable epoxy resin prepared in Example 1 has good self-healing ability because the overlapped sections of broken samples have fused together as entirety via the exchange reaction between dynamic disulfide linkages.

FIG. 8 gives original (a) and self-healed (b) stress-strain curves and images under tensile lap shear tests of self-healable epoxy resin prepared in Example 1. According to ISO 4587: 2003, the prepolymer of self-healable epoxy resin prepared in Example 1 was cast on one plate, which was then covered by another plate with an overlapped length of 12.5 mm. After that, the sample was cured following the protocol, and the resultant sample was acted as the original sample. On the other hand, two plates cast with prepolymer were separately cured first and then held together tightly by clamps and maintained at 160° C. for 1 h, the resultant sample was taken as the self-healed sample. As shown in FIG. 8, the shear strengths of original sample and self-healed sample measured by tensile lap shear tests are 5.24±0.43 and 5.05±0.26 MPa, respectively, so the healing efficiency of self-healable epoxy resin prepared in Example 1 is calculated to be above 95%.

Figure 9:
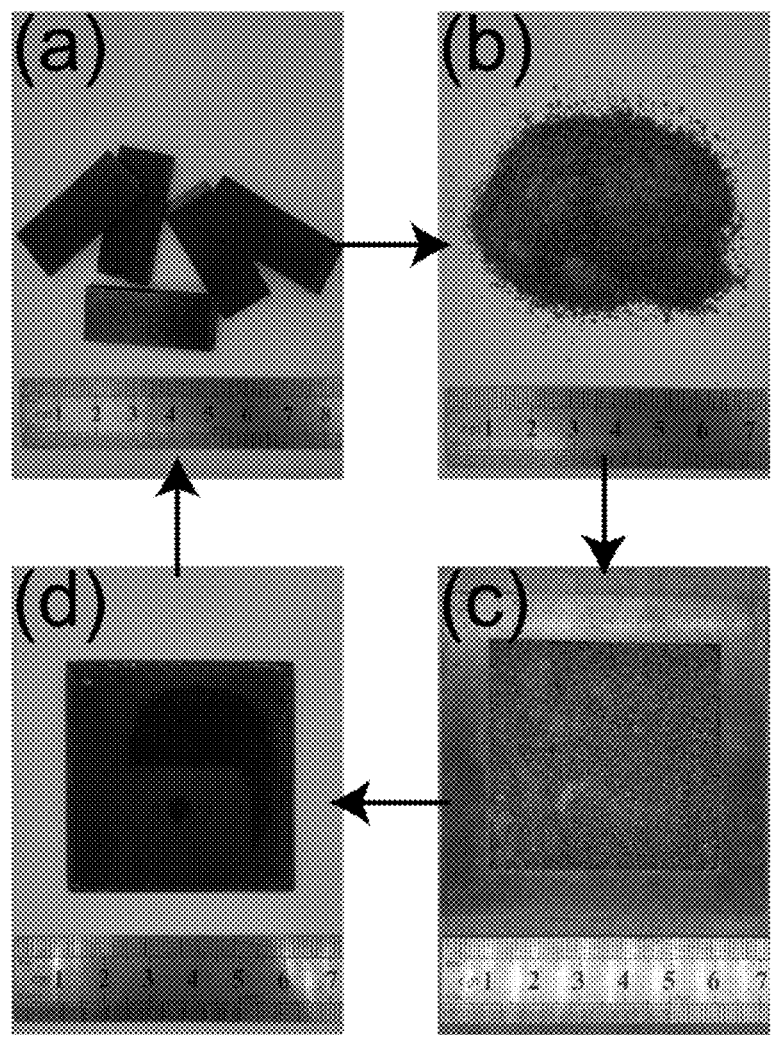
FIG. 9 is digital images of recycling and remolding process of self-healable epoxy resins synthesized in Example 14 of this invention.

FIG. 9 gives digital images of recycling and remolding process of self-healable epoxy resins prepared in Example 1. Cured self-healable epoxy resins prepared in Example 1 were completely ground into fine powders (FIG. 9b) using a pulveriser, which were then transferred into a square mold, and the mold was pressed under a pressure of 1 MPa, followed by heating and maintaining at 160° C. for 1 h in a molding machine, successively, to get square panel without observable cracks (FIG. 9d), clearly demonstrating that ground self-healable epoxy resin powders have been bonded together through the topology rearrangement based on the exchangeable feature of dynamic disulfide bonds. This result provides a clear evidence of good self-healing ability, recyclability and remoldability for self-healable epoxy resins prepared in this invention.

FIG. 10 gives FTIR spectra of original and remolded self-healable epoxy resin prepared in Example 1. The characteristic vibrations of carbonyl (1730 $cm^{-1}$) and C—S (1412 $cm^{-1}$) are visible, indicating that esters and disulfide groups remain in the network, that is, no detectable structural change takes place during the whole process of grind-remolding and heat treatment at 160° C. for remolded self-healable epoxy resin prepared in Example 1.

FIG. 11 gives DMA curves of original and remolded self-healable epoxy resin prepared in Example 1. The remolded sample has $T_g$ of 110° C. and 92% of the storage modulus at glassy state; meanwhile, the intensity and width of tan δ peak severally increases and narrows because the chemical structure of the network is refurbished, which means the chain mobility of remolded sample strengthens and its stiffness weakens.

The above-mentioned results indicate that the chemical structure and thermal property of self-healable epoxy resins prepared in Example 1 remain during the grind-remolding process, which is beneficial for the recycling and remolding process. In this invention, with the catalyst of potassium iodide, an ester solution of 2-mercaptoacetic acid was oxidated by 30 wt % $H_2O_2$ to form 2,2'-dithiodiacetic acid; then 2,2'-dithiodiacetic acid was dehydrated by anhydride to form 1,4,5-oxadithiepane-2,7-dione; 1,4,5-oxadithiepane-2,7-dione and methylhexahydrophthalic anhydride were mixed by mass ratio and cured with epoxides to get a kind of self-healable epoxy resins. Through controlling dynamic and permanent three-dimensional crosslinked network, the self-healable epoxy resins provided in this invention exhibit high thermal resistance and improved mechanical properties as well as excellent self-healing ability, recyclability and remoldability. This invention provides a preparation method with the merits of low cost, simple production processes, broad application prospects and strong utility.

The invention claimed is:

1. A method for preparing a self-healable epoxy resin, comprising:
   (1) by mass, at 20 to 30° C., 120 parts of 2-mercaptoacetic acid, 500 to 700 parts of ester solvent and 0.6 to 1.2 parts of potassium iodide are mixed homogeneously to obtain a solution; 80 to 90 parts of 30 wt % $H_2O_2$ are added dropwise to the solution and continued to react for 2 to 4 h to get 2,2'-dithiodiacetic acid;
   (2) by mass, at 20 to 30° C., 100 parts of 2,2'-dithiodiacetic acid and 120 to 150 parts of anhydride are mixed homogeneously and continued to react for 2 to 4 h to get 1,4,5-oxadithiepane-2,7-dione;
   (3) by mass, at 50 to 70° C., 100 parts of epoxy resin, 42 to 84 parts of 1,4,5-oxadithiepane-2,7-dione and 0 to 43 parts of methylhexahydrophthalic anhydride are mixed homogeneously, after curing, the self-healable epoxy resin is obtained.

2. The method according to claim 1, wherein the ester solvent is methyl acetate, ethyl acetate, propyl acetate, methyl propionate, ethyl propionate, or any combination thereof, and the anhydride is acetic anhydride, trifluoroacetic anhydride, or any combination thereof.

3. The method according to claim 1, wherein the epoxy resin is glycidyl ether type epoxy resin, glycidyl ester type epoxy resin, glycidyl amine type epoxy resin, aliphatic epoxides, alicyclic epoxides, or any combination thereof.

* * * * *